United States Patent [19]

Lueck

[11] 4,133,641

[45] Jan. 9, 1979

[54] COMBUSTION CONE FOR CHEMICAL ANALYSIS INSTRUMENT

[75] Inventor: Dale E. Lueck, Chelmsford, Mass.

[73] Assignee: Ionics Inc., Watertown, Mass.

[21] Appl. No.: 895,426

[22] Filed: Apr. 12, 1978

[51] Int. Cl.² ............................................. G01N 25/24
[52] U.S. Cl. ................................. 422/78; 23/230 PC
[58] Field of Search ........ 23/253 PC, 230 PC, 254 R; 73/23

[56] References Cited

U.S. PATENT DOCUMENTS

| | | | |
|---|---|---|---|
| 3,776,695 | 12/1973 | Peterson | 23/230 PC |
| 3,933,429 | 1/1976 | Shibata et al. | 23/253 PC |
| 4,023,932 | 5/1977 | Cohen | 23/253 PC |
| 4,066,402 | 1/1978 | Komiyama | 23/230 PC |

Primary Examiner—R.E. Serwin
Attorney, Agent, or Firm—Norman E. Saliba

[57] ABSTRACT

A high thermal conductivity combustion cone in combination with a chemical analysis instrument is disclosed. The cone functions to capture and rapidly volatilize a liquid sample drop injected into the instrument. The volatilized components are then reacted with a feed or carrier gas in the presence of a heated catalyst bed. Changes in the reacted gas are detected by a sensor and quantitatively analyzed as an indicator of the chemical nature of the sample.

8 Claims, 1 Drawing Figure

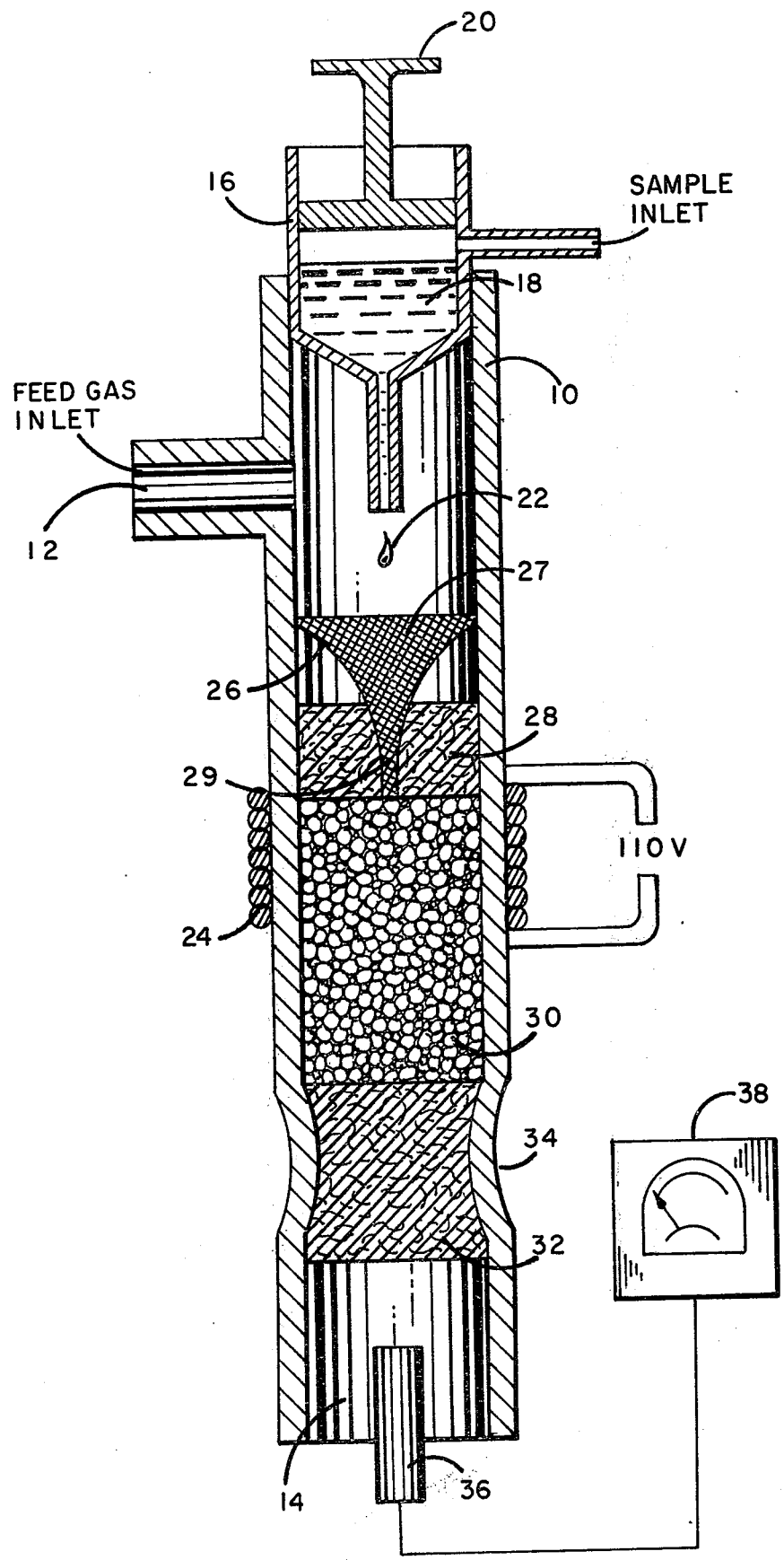

COMBUSTION CONE FOR CHEMICAL ANALYSIS INSTRUMENT

BACKGROUND OF THE INVENTION

1. Field of the Invention

The invention resides in the field of chemical analysis instruments and more particularly relates to those devices which react a carrier gas with a volatilized liquid sample in the presence of a catalyst to produce a chemical change in the composition of the gas stream.

2. Description of the Prior Art

Chemical analysis instruments of the type for which the invention is intended are well known and described in the prior art. The function of these devices is to determine a particular composition of a substance by reacting within a reaction chamber a volatilized sample of the substance with a feed or carrier gas stream in a catalyst bed and then measuring one or more parameters of the reacted gas stream as an indicator of its composition.

A detailed description of such a device is found in U.S. Pat. No. 3,567,385, C. E. VanHall, in which an apparatus and method for determining total oxygen demand (TOD) of a substance is described. The oxygen demand of a material containing oxidizable components is determined by the combustion of a small sample of the material in a continuous stream of carbon dioxide within a heated catalyst bed. Carbon monoxide produced as a result of the combustion relates directly to the TOD of the sample which can thus be indirectly measured by a quantitative analysis of the reacted gas stream for carbon monoxide content. A particularly useful application of TOD measurement is the determination of pollution levels in water systems and waste streams. Other patents, such as U.S. Pat. Nos. 3,530,292, 3,560,156 and 3,840,341, which disclose apparatus and methods for measuring carbon or oxygen demand in liquid samples by the combustion method, may also utilize the present invention.

Since the measurements involved are quantitative, accuracy and reproducibility depend upon the physical characteristics and functional operation of the apparatus. Hence the size of the sample, particularly a liquid sample, and the rate of volatilization are among the critical parameters which must be closely controlled in order to provide meaningful measurements.

In accordance with this requirement, the present invention is directed toward a means for rapidly and completely volatilizing a liquid drop sample in a TOD or similar combustion analysis instrument.

SUMMARY OF THE INVENTION

The invention may be summarized as a high thermal conductivity combustion cone, preferably comprised of a foraminous, porous, or mesh type metal or alternatively a ceramic material such as aluminum oxide. The cone is used in combination with a chemical combustion analysis instrument and is employed to capture and rapidly volatilize a liquid sample drop for subsequent reaction with a carrier gas in the presence or a catalyst bed.

In the instruments to which the invention is applicable, the introduction of a sample to be analyzed is accomplished by the injection of a small drop of liquid, for example water containing impurities, into a heated stream of reactive gas in close proximity to a high temperature catalyst bed. The volatilized sample components react with the gas stream causing a change in the composition of the stream which may be detected or monitored by an appropriate sensor.

In prior art devices, the method of introducing the sample into the instrument, i.e. injection directly into the gas stream, often results in a spacial separation of sample components due to differences in volatility of the components and a relatively slow rate of vaporization as compared to the downstream detector or sensor response. Comparatively slow volatilization results in a stretching out of the sample-gas stream reaction and a concurrent blurring of sensor response. This is particularly critical when the value of peak sensor response is used as an indicator of the sample component to be measured. The present invention is therefore intended to yield a rapid and reproducable combustion of sample components by providing a means of capturing a liquid sample drop in contact with a hot surface with high thermal conductibility and sufficient thermal content to rapidly and completely volatilize the liquid sample.

The invention will be more clearly understood from the description of the preferred embodiment and drawing which follow.

DESCRIPTION OF THE DRAWING

The drawing is a schematic representation of a combustion analysis instrument employing the invention.

DESCRIPTION OF THE PREFERRED EMBODIMENT

Referring to the drawing, there is shown a combustion chamber conduit 10 having a feed or carrier gas inlet 12 and an exhaust outlet 14. A calibrated sample injector 16 is positioned at the upper end of the conduit tightly sealed to the wall of the conduit to prevent the escape of feed gas. The injector contains a sample 18 of the liquid to be analyzed and by depressing plunger 20 a sample drop 22 of known volume is dispensed into the gas stream. Various other means for metering precise amounts of a liquid for passage into a combustion tube are well known in the art and may be employed in the practise of the present invention.

The combustion or reaction chamber 10 and the instrument components contained therein are heated by any convenient means, an electric coil 24 for example. Combustion cone 26 formed of a high thermal conductivity material such as platinum screen or a ceramic is positioned in the conduit to capture the falling sample drop 22 in the frustum 27 of the cone. The cone is held in place by a heat resistant material 28 such as Fiberfrax, a ceramic fiber material, obtainable from and trademarked by the Carborundum Co., Niagra Falls, N.Y., and is heated by heat transfer from the coil, conduit, and catalyst bed.

The apex of the cone, which is preferably of a size approximately equal to the size of the sample drop, is placed just above or in contact with catalyst bed 30 held in place by an additional quantity 32 of Fiberfrax which is held in place by the neck 34 of the conduit.

The cone functions to more rapidly and completely volatilize the sample drop and its components by forcing the drop as it approaches the apex into close and complete contact with the heated surface of the cone.

The volatilized sample components are then swept into the catalyst bed by the feed gas where they react with the gas to produce a chemical change which is detected by sensor 36 located at the outlet 14 of the conduit. The reaction of the sensor may be monitored and recorded by an appropriate measuring instrument 38.

Having described the invention in a generalized embodiment, the following example shows the results obtained using apparatus with and without the combustion cone and further illustrates the usefulness and practicality of the concept. Five dispersions of combustible compounds containing 50 p.p.m. of total oxygen demand (T.O.D.) were analyzed with 10 successive readings made on each solution. The results shown in the table below give the mean reading in p.p.m. of T.O.D. and the standard deviation obtained. It is readily noted that the use of the combustion cone of the present invention gave the more accurate results.

TABLE

| material | without combustion cone | with combustion cone |
| --- | --- | --- |
| *KHP | 50.0 ± 1.1 | 50.0 ± 0.7 |
| Acetic Acid | 62.6 ± 1.8 | 50.0 ± 0.5 |
| Ethanol | 80.5 ± 2.4 | 50.7 ± 0.6 |
| Phenol | 66.7 ± 2.9 | 48.9 ± 2.5 |
| KHP/Ethanol mixture | 50.8 ± 2.9 | 46.1 ± 0.5 |
| Mean, all solutions = 62.1 ± 12.6 | | 49.1 ± 1.8 |

*Potassium Acid Phthalate

Since certain changes may be made in the above apparatus without departing from the scope of the invention herein involved, it is intended that all matter contained in the above description as shown in the accompanying drawing shall be interpreted as illustrative and not in a limiting sense.

The embodiments of the invention in which an exclusive property of privilege is claimed are defined as follows:

1. In a chemical combustion analysis instrument wherein a liquid sample drop is volatilized in the presence of a carrier gas for reaction with said gas within a heated catalyst bed, the improvement which comprises:

A combustion cone of high thermal conductivity positioned to receive said liquid sample drop at the frustum of said cone and to eject said sample in a volatilized state at the apex of said cone, said apex positioned in close proximity to said catalyst bed.

2. The apparatus of claim 1 therein the apex of said cone is approximately the size of the liquid sample drop.

3. The apparatus of claim 2 wherein said cone is comprised of platinum screen.

4. The apparatus of claim 2 wherein said cone is comprised of ceramic.

5. A chemical combustion analysis instrument for analyzing a liquid sample comprising in combination:
 a. a combustion conduit having an inlet end and an outlet end;
 b. a catalyst bed positioned within said conduit;
 c. means for injecting a liquid sample drop into said conduit at said inlet end;
 d. a combustion cone positioned within said conduit upstream from and in close proximity to said catalyst bed, said cone arranged to capture and volatilize said sample drop;
 e. means for heating said cone, said conduit, and said bed;
 f. means for passing a gas through said conduit; and
 g. sensor means positioned at the outlet end of said conduit for measuring changes in the composition of said gas as a result of the combustion of said sample drop in said conduit.

6. The apparatus of claim 5 wherein the apex of said cone is in contact with said catalyst bed and said apex is approximately the size of the liquid sample drop.

7. The apparatus of claim 6 wherein said cone is comprised of platinum screen.

8. The apparatus of claim 6 wherein said cone is comprised of ceramic.

* * * * *